(12) United States Patent
Komuda et al.

(10) Patent No.: US 11,648,356 B2
(45) Date of Patent: May 16, 2023

(54) SAFETY NEEDLE DEVICES

(71) Applicant: HTL-STREFA S.A., Ozorków (PL)

(72) Inventors: Marcin Komuda, Ozorków (PL);
Marcin Niemiec, Ozorków (PL);
Robert Grzelak, Ozorków (PL);
Robert Osak, Ozorków (PL); Rafał Perłak, Ozorków (PL); Bartłomiej Białas, Ozorków (PL)

(73) Assignee: HTL-STREFA S.A., Ozorków (PL)

( * ) Notice: Subject to any disclaimer, the term of this patent is extended or adjusted under 35 U.S.C. 154(b) by 98 days.

(21) Appl. No.: 17/327,252

(22) Filed: May 21, 2021

(65) Prior Publication Data
US 2021/0369978 A1 Dec. 2, 2021

(30) Foreign Application Priority Data

May 28, 2020 (EP) ..................... 20177261

(51) Int. Cl.
*A61M 5/32* (2006.01)
*A61M 5/50* (2006.01)

(52) U.S. Cl.
CPC ........ *A61M 5/3271* (2013.01); *A61M 5/3293* (2013.01); *A61M 5/50* (2013.01); *A61M 5/5086* (2013.01); *A61M 2005/3247* (2013.01)

(58) Field of Classification Search
CPC .... A61M 5/50; A61M 5/5086; A61M 5/3271; A61M 2005/3247; A61M 5/3293; A61M 2005/3267; A61M 5/326; A61M 5/3272; A61M 5/321; A61M 5/3213
See application file for complete search history.

(56) References Cited

U.S. PATENT DOCUMENTS

| | | | |
|---|---|---|---|
| 2009/0030376 A1 | 1/2009 | Teufelberger et al. | |
| 2009/0227956 A1 | 9/2009 | Emmott et al. | |
| 2021/0038830 A1* | 2/2021 | Grzelak | A61B 10/0233 |

FOREIGN PATENT DOCUMENTS

| | | |
|---|---|---|
| WO | 2012003516 A2 | 1/2012 |
| WO | 2012003516 A3 | 1/2012 |
| WO | 2019156579 A1 | 8/2019 |

OTHER PUBLICATIONS

European Extended Search Report in corresponding EP Application No. 20177261.3, dated Nov. 18, 2020, 9 pages.

* cited by examiner

*Primary Examiner* — Theodore J Stigell
*Assistant Examiner* — Rachel T. Smith
(74) *Attorney, Agent, or Firm* — MH2 Technology Law Group LLP

(57) ABSTRACT

A safety needle device may include: a hub configured to be connected to a vessel; a needle attached to the hub, the needle extending between a distal end, configured for insertion into a patient, and an opposed proximal end, configured for connection to the vessel; a shield slidable relative to the hub and rotationally constrained, wherein the shield is irreversibly slidable from an initial position, before injection, to a locking position, after injection, passing through an intermediate position; a housing attached to the hub and surrounding: a portion of the hub, a portion of the shield when the shield is in the initial position and in the locking position, and almost totally the shield when the shield is in the intermediate position; and an elastic member biased to push the shield toward the distal end and to resist a longitudinal sliding of the shield toward the proximal end.

12 Claims, 7 Drawing Sheets

SAFETY NEEDLE DEVICES

CROSS-REFERENCE TO RELATED APPLICATION(S)

This application claims priority under 35 U.S.C. § 119 from European Patent Application No. 20177261.3, filed on May 28, 2020, in the European Patent Office ("EPO"), the entire contents of which are incorporated herein by reference.

BACKGROUND OF INVENTION

Field of Invention

The invention relates to the technical field of a medical device, in particular to a protection device able to prevent the user from accidental or intentional injuries with a needle before and after the injection.

Background of the Invention

Typically, a safety needle device comprises an elongated needle having a first end insertable into the patient's skin and a second end insertable into a vessel for supplying a substance. The needle is embedded in a hub and partially surrounded by a housing fixed to the hub. Known device also comprise a shield surrounding the needle and moving along the needle. The shield has a first end directed toward the outside of the housing and a second end moving inside the housing and directed toward the hub. A spring is arranged between the shield and the hub such that the shield in constantly pushed toward the first end of the needle. Specifically, during the injection, the shield is pushed inside the housing toward the second end of the needle, compressing the spring. Then, during the extraction of the needle from the patient, the spring pushes the shield toward the first end of the needle. For preventing further uses or injuries, the device comprises a locking means able to lock the sliding of the shield after the injection.

One example of the safety needle device is disclosed in the patent application WO 2019/156579 A1 in the name of the Applicant. Such device comprises a rotational sleeve inside the housing which surrounds at least partially the needle. Specifically, the shield and the rotational sleeve cooperate in order to lock the shield for preventing further uses or injuries. In detail, at least the second end of the shield is inserted into the rotational sleeve and a pin projecting from the outer surface of the shield engages a groove formed on the rotational sleeve. Initially, the pin is arranged in a first bay formed on the groove which allows the longitudinal movements of the shield. During the injection, the shield slides inside the rotational sleeve causing a first rotation of the sleeve then during the extraction the shield is pushed at least partially outside the sleeve by the spring causing a second rotation of the sleeve. The rotations allow the pin to be routed from the first bay to a second bay which locks the pin preventing further longitudinal movements of the shield.

However, the known safety needle devices show some drawbacks. In fact, such devices do not ensure the correct protection to the user from further uses and from accidental injuries. Furthermore, known devices are complex and need a lot of elements in order to achieve the results, increasing the overall costs of the production and design.

It is to be noted also that the device disclosed in the WO 2019/156579 A1 in order to prevent the rotation of the shield during the injection has ribs formed on the hub engaged by the shield when the latter enters in the rotational sleeve during the injection. Such ribs could prevent the longitudinal motion of the shield if not correctly aligned with corresponding grooves on the shield making the device useless.

SUMMARY OF INVENTION

In this context, the technical task underlying the present invention is to propose a safety needle device which overcome the drawbacks of the above prior art.

Specifically, it is an object of the present invention to provide a safety needle device able to ensure the protection to the user and at the same time to improve the availability of the device itself.

The technical task set out and the specified objects are substantially achieved by a shield interposed between the housing and a sleeve which surrounds the hub.

BRIEF DESCRIPTION OF THE DRAWINGS

The present invention will now be described in more detail hereinafter with reference to the accompanying drawings, in which some embodiments of the invention are shown.

DETAILED DESCRIPTION

Figure 1:
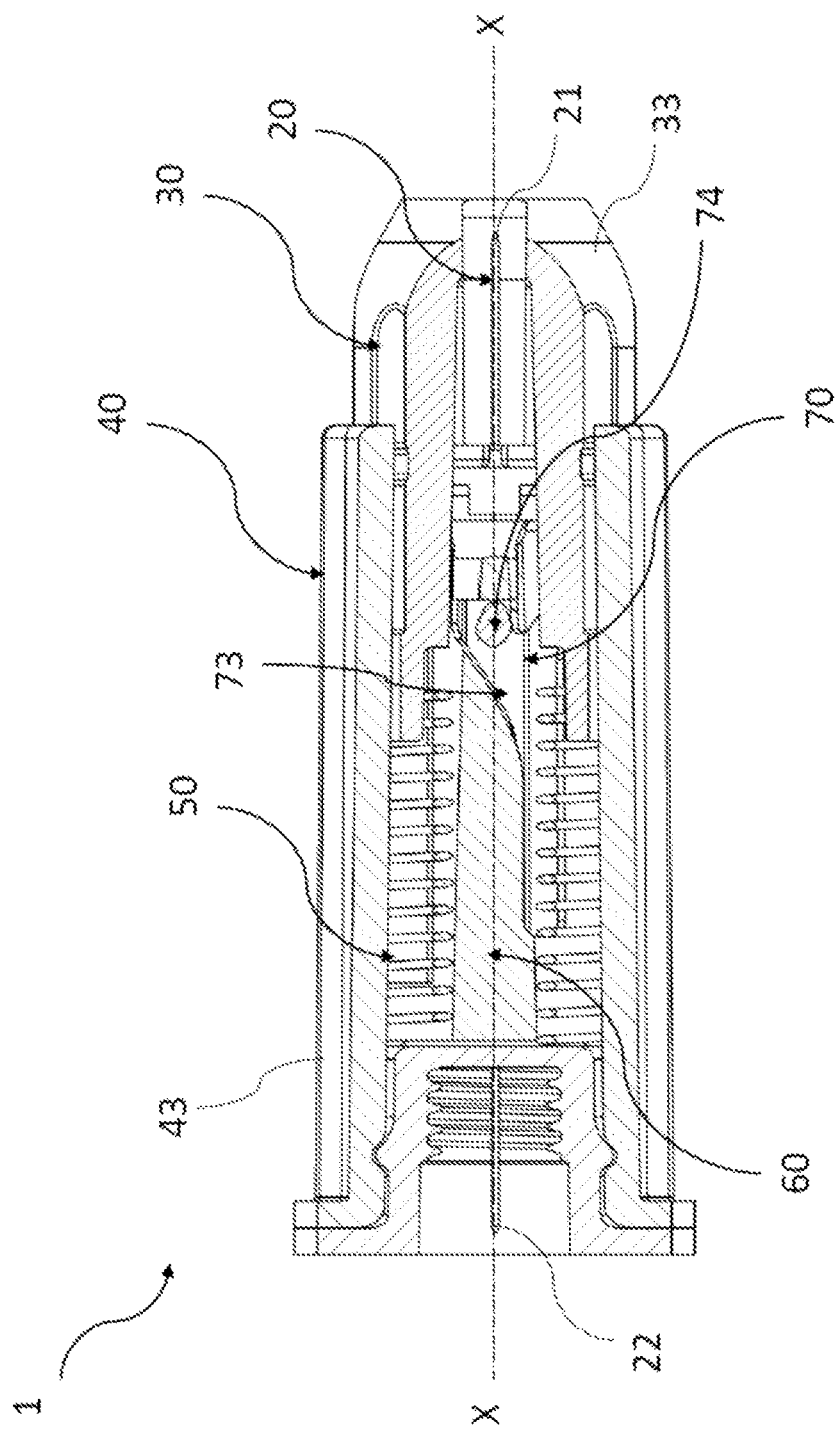
FIG. 1 is a first section view of the safety needle device according to one embodiment of the present invention.
Figure 2:
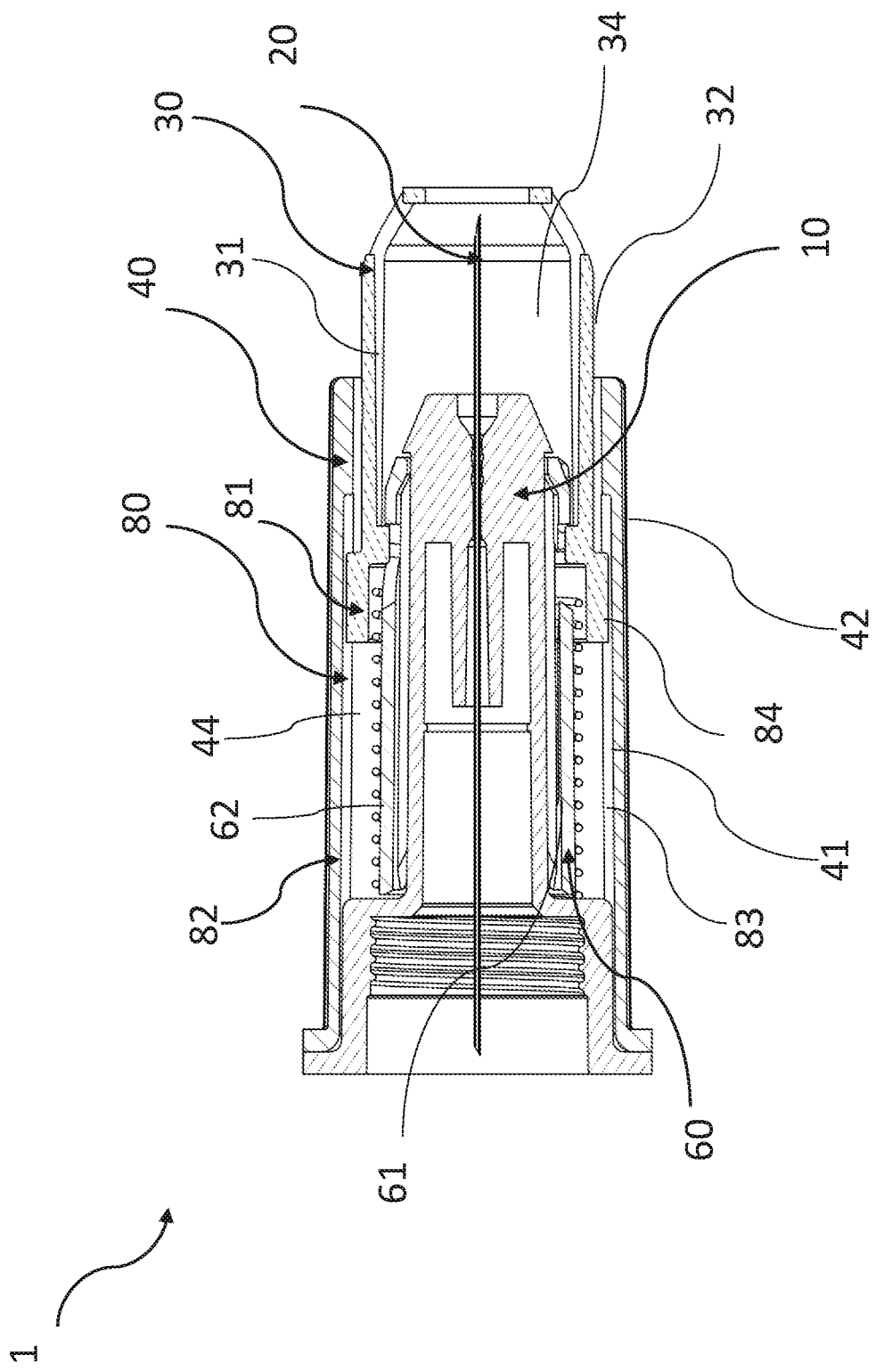
FIG. 2 is a second section view of the safety needle device according to one embodiment of the present invention.
Figure 3:
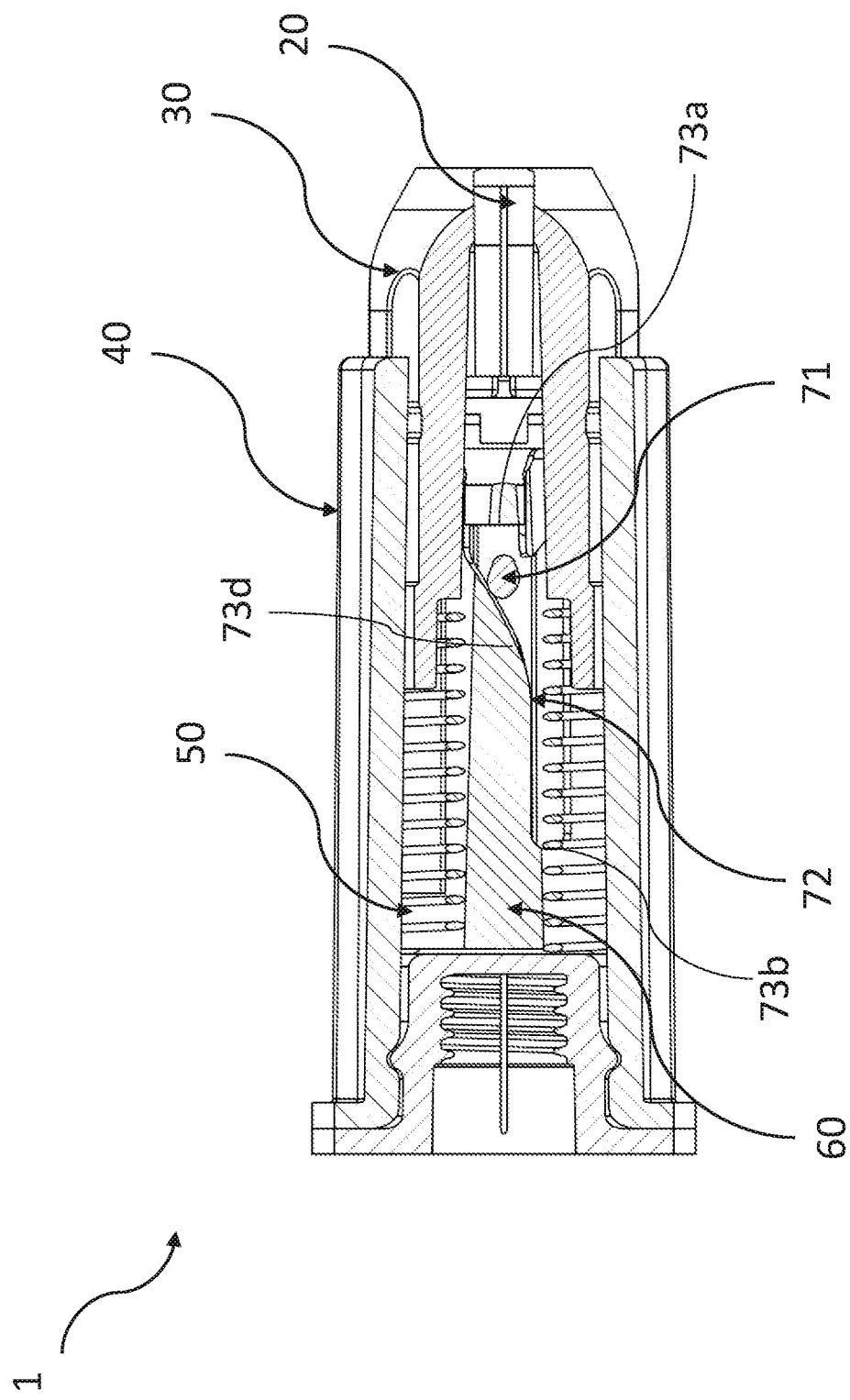
FIG. 3 is a section view of the safety needle pen of FIG. 1 and FIG. 2 during a first stage of injection.
Figure 4:
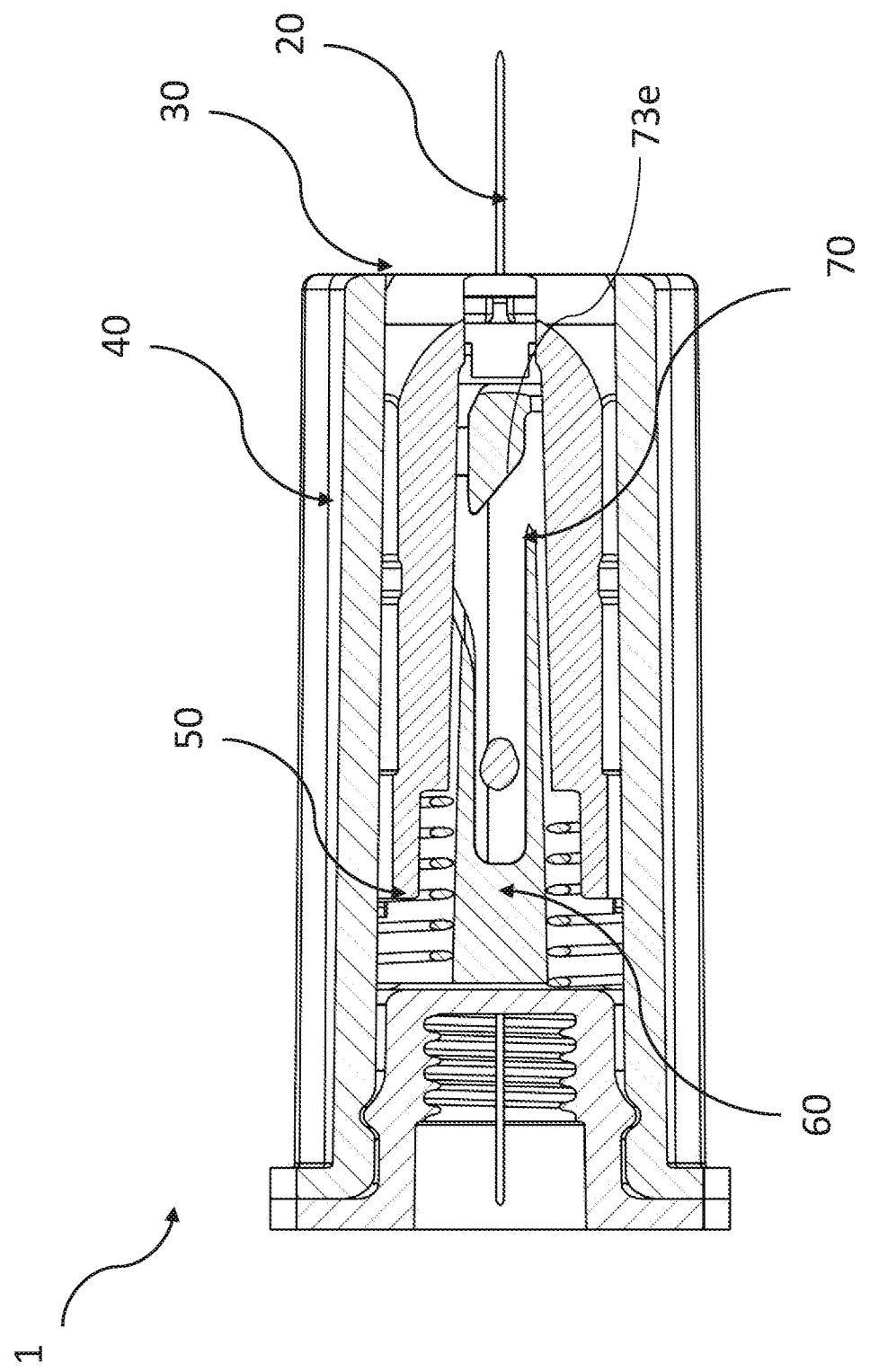
FIG. 4 is a section view of the safety needle pen of FIG. 1 and FIG. 2 during a second stage of injection.
Figure 5:
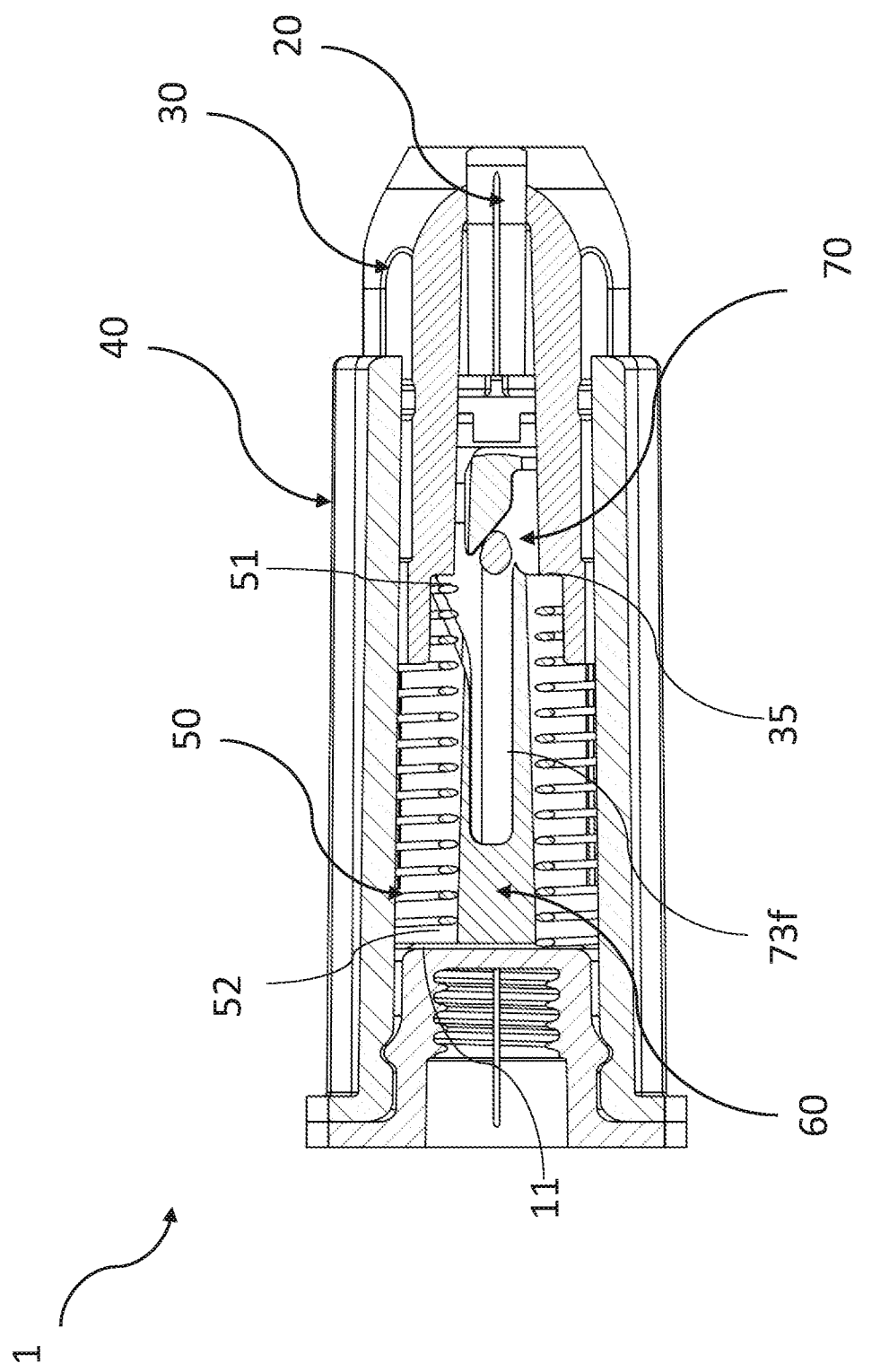
FIG. 5 is a section view of the safety needle pen of FIG. 1 and FIG. 2 during a third stage of injection.
Figure 6:
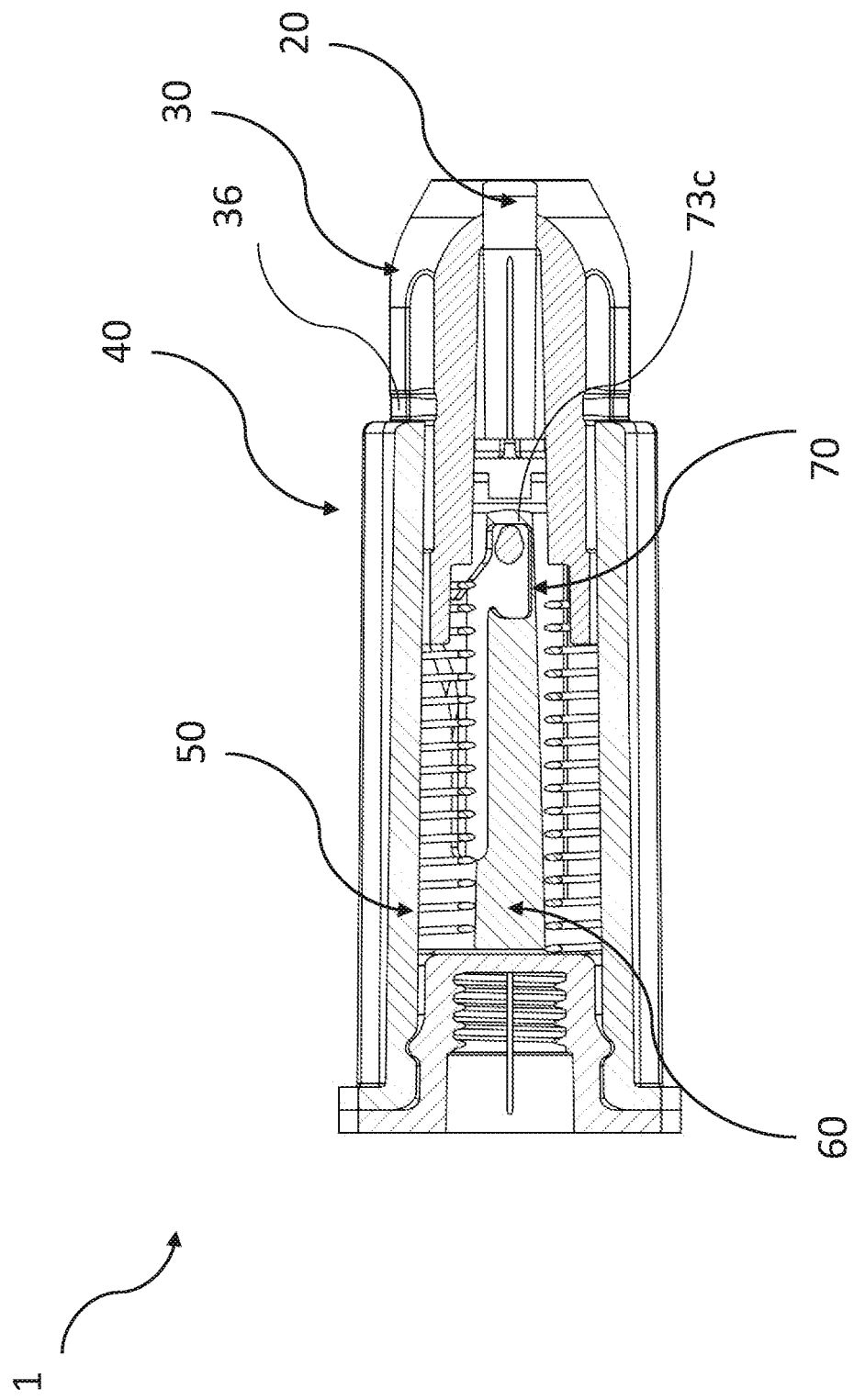
FIG. 6 is a section view of the safety needle pen of FIG. 1 and FIG. 2 in a locking configuration.
Figure 7:
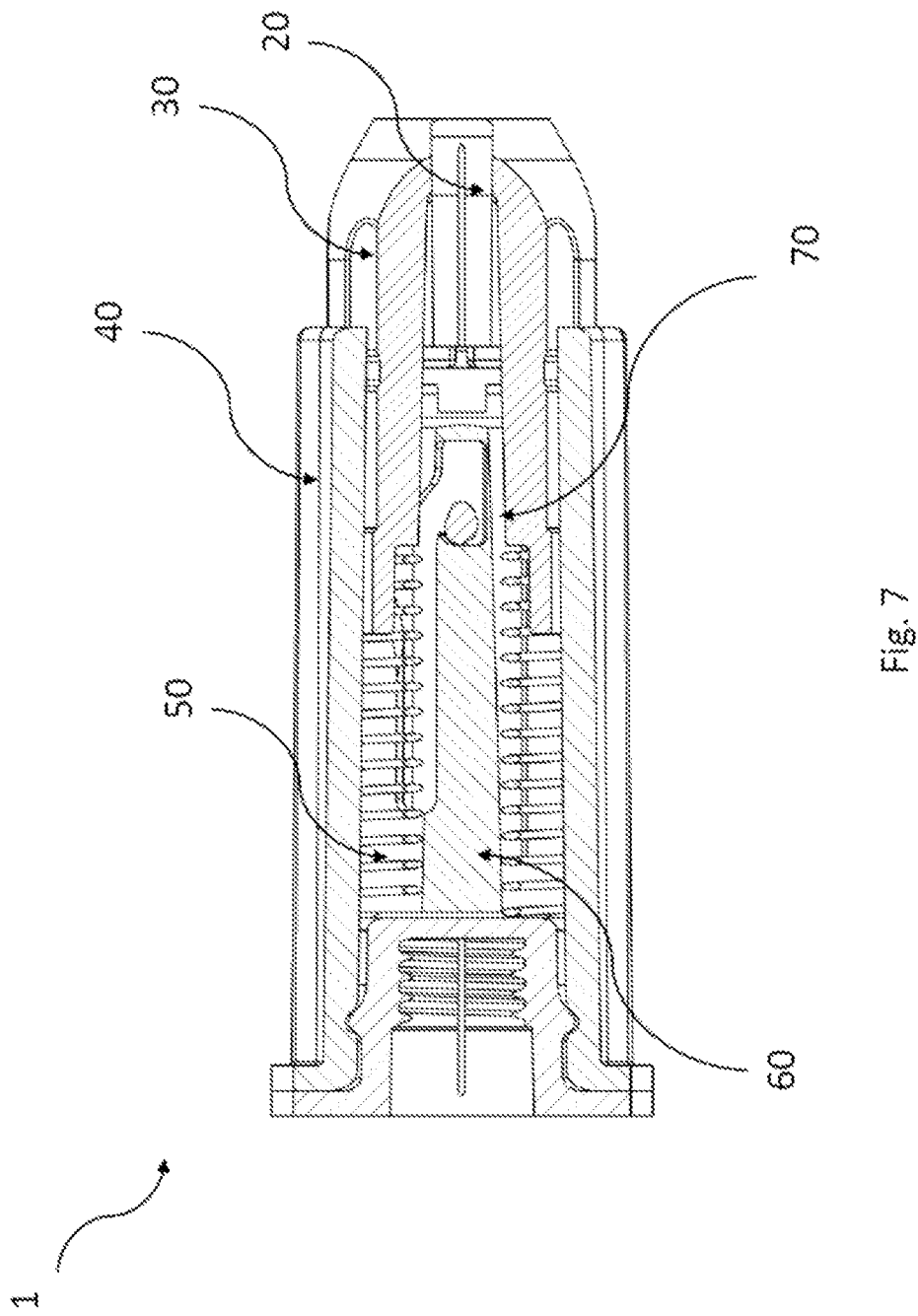
FIG. 7 is a section view of the safety needle pen of FIG. 1 and FIG. 2 in a locking configuration.

With reference to FIGS. 1-7, a safety needle device is indicated as a whole by numeral 1. Safety needle device 1 can be associated to a vessel containing a substance to inject into a patient or filled by blood withdraw from the patient.

The safety needle device 1 comprises a hub 10 configured to be connected to the vessel and a needle 20 attached to the hub 10. The needle 20 extends along a longitudinal axis X-X between a distal end 21, formed to be inserted into a patient, and opposed proximal end 22 formed to be connected to the vessel.

The safety needle device 1 comprises a shield 30 slidable along the longitudinal axis X-X relative to the hub 10 between an initial position, before the injection, to a locking position after injection, passing through an intermediate position. Specifically, during the injection of the needle into the patient, the shield 30 passes from the initial position to the intermediate position, sliding toward the proximal end 22 of the needle 20 along the longitudinal axis X-X. In contrast, during the extraction of the needle from the patient, the shield 30 passes from the intermediate position to the locking position, sliding toward the distal end 21 of the needle 20 along the longitudinal axis X-X.

According to a preferred embodiment, the shield 30 is configured to cover and protect the distal end 21 of the needle both in initial position and in locking position. Specifically, the shield 30 is configured to be locked in the locking position avoiding further sliding to uncover the distal end 21 of the needle after an injection.

Preferably, the shield 30 is rotationally constrained around the longitudinal axis X-X.

More preferably, the shield 30 comprises a tubular body 33 extending along the longitudinal axis X-X defining a passing through channel 34 into which is inserted at least partially the hub 10.

It is to be noted that the shield 30 has an inner surface 31 facing inwardly toward the hub 10 and an opposed outer surface 32 facing outwardly. Specifically, the tubular body 33 has the inner surface 31 facing the passing through channel 34.

According to one embodiment, the shield 30 has a sign 36 on the outer surface 32 configured to indicate the state of use of the safety needle device. Specifically, the sign 36 is formed such that it is visible when the shield 30 has passed from the initial position to the locking position.

The safety needle device 1 comprises a housing 40 attached to the hub 10 and surrounding a portion of the hub 10, a portion of the shield 30 when the shield 30 is in the initial and locking position and almost totally, preferably totally the shield 30 when the shield 30 is in the intermediate position. Preferably, the housing 40 comprises a tubular body 43 having a passing through channel 44. Specifically, the shield 30 is at least partially inserted into the passing through channel 44 in the initial position. In addition, the shield 30 is almost totally, preferably totally, inserted into the passing through channel 44 in the intermediate position. In detail, the shield 30 comprises a first length portion inserted in the passing through channel 44 in the initial position; and a second length portion inserted in the passing through channel 44 in the locking position, wherein the first portion is equal or longer than the second portion. The shield 30 further comprises a third length portion inserted in the passing through channel 44 in the intermediate position, wherein the third portion is longer than the first and second length portions. Preferably, the length of the third length portion is equal to the length of the shield 30.

Preferably, the housing 40 has an inner surface 41 facing at least partially the shield 30 and an opposed outer surface 42 facing outwards. More preferably, the inner surface 41 of the housing 40 is partially facing the outer surface 32 of the shield 30. It is to be noted that tubular body 43 has the inner surface 41 of the housing 40 facing the passing through channel 44 of the housing.

The safety needle device 1 comprises a guiding arrangement 80 configured to guide the shield 30 along the longitudinal axis X-X between the initial position and the locking position preventing relative rotation of the shield 30 with respect to the housing 40 and to the hub 10. Specifically, the guiding arrangement 80 comprises first guiding members 81 formed on the shield 30 and second guiding members 82 formed on the housing 40. In detail, the first guiding members 81 are configured to cooperate with the second guiding members 82 to guide the sliding of the shield 30 along the longitudinal axis X-X and to prevent rotation of the shield 30 relative to the housing 40.

Preferably, the first guiding members 81 are formed on the outer surface 32 of the shield 30 while the second guiding members 82 are formed on the inner surface 41 of the housing 40.

More preferably, the second guiding members 82 comprise longitudinal grooves 83 formed on the inner surface 41 of the housing 40. Specifically, the longitudinal grooves 83 are rectilinear and extend along the longitudinal axis X-X. Instead, the first guiding members 81 comprise protrusions 84 projecting from the outer surface 32 of the shield 30 and configured to engage the longitudinal grooves 83. Such engagement is constantly maintained from the initial position to the locking position of the shield 30.

Even more preferably, the first guiding members 81 are angularly spaced apart on the outer surface 32 of the shield 30 and the second guiding members 82 are angularly spaced apart on the inner surface 41 of the housing 40.

The safety needle device 1 comprises an elastic member 50 arranged within the housing and acting on the shield 30. Preferably, the elastic member 50 is configured to constantly urge the shield 30 toward the distal end 21 of the needle 20. Specifically, the elastic member 50 is biased to push the shield 30 toward the distal end 21 of the needle 20 and to resist a longitudinal sliding of the shield 30 toward the proximal end of the needle 20. In detail, the elastic member 50 is configured to be elastically compressed during the injection with the passage of the shield 30 from the initial position to the intermediate position and to be elastically extended during the extraction with the passage of the shield 30 from the intermediate position to the locking position.

Preferably, the elastic member 50 is interposed between the hub 10 and the shield 30 in order to constantly urge the shield 30. Specifically, the hub 10 comprises a stop wall 11 configured to accommodate a portion of the elastic member 50. In contrast, the shield 30 comprises an annular flange 35 projecting from the inner surface 31 of the shield 30 and configured to retain the distal portion 51 of the elastic member 50.

More preferably, the elastic member 50 extends between distal portion 51 and a proximal portion 52 along the longitudinal axis X-X. Accordingly, the stop wall 11 accommodates the proximal portion 52 of the elastic member 50 and the annular flange 35 accommodates the distal portion 51 of the elastic member 50.

The safety needle device 1 comprises a sleeve 60 arranged within the housing 40 and rotatably mounted around the longitudinal axis X-X relative to the shield 30 and the housing 40. Specifically, the sleeve 60 at least partially surrounds the hub 10 and is configured to rotate around the longitudinal axis X-X relative to the hub 10.

Specifically, the sleeve 60 has inner surface 61 facing the hub 10 and an opposite outer surface 62 facing outwards at least partially the inner surface 41 of the housing 40.

According to one embodiment, the shield 30 surrounds at least partially the sleeve 60 when the shield 30 is in the initial position and in the locking position. While the shield 30 surrounds almost totally, preferably totally, the sleeve 60 when the shield 30 is in the intermediate position. In detail, the sleeve 60 is at least partially inserted into the passing through channel 34 of the shield 30 when the shield 30 is in the initial position and in the locking position. Instead, the sleeve 60 is inserted almost totally, preferably totally, into the passing through channel 34 of the shield 30 when the shield 30 is in the intermediate position. More in detail the first length portion and the second length portion of the shield 30 surround at least partially the sleeve 60 respectively in the initial and locking positions. Instead, the third length portion of the shield 30 surrounds almost totally, preferably totally, the sleeve 60 respectively in the intermediate position.

It is to be noted that, the inner surface 41 of the housing 40 is fact at least partially facing the sleeve 60 and the shield 30. Moreover, the inner surface 31 of the shield 30 is partially facing the sleeve 60 and the outer surface 32 of the shield 30 is partially facing the inner surface 41 of the housing 40. Accordingly, the inner surface 61 of the sleeve 60 is partially facing the hub 10 and the opposite outer surface 62 is partially facing the inner surface 31 of the shield 30 and to the inner surface 41 of the housing 40.

Advantageously, the relationship between the inner surfaces 31, 41, 61 and the outer surfaces 32, 42, 62 are maintained in the initial position, intermediate position and locking position of the shield 30.

According to a preferred embodiment, the elastic member 50 at least partially surrounds the sleeve 60. Specifically, the elastic member 50 surrounds the outer surface 62 of the sleeve 60.

The safety needle device 1 comprises a locking arrangement 70 configured to rotate the sleeve 60 upon sliding of the shield 30 and to lock the shield 30 in the locking position. Specifically, the locking arrangement 70 comprises at least a first locking member 71 formed on the shield 30 and at least a second locking member 72 formed on the sleeve 60. Preferably, the first locking member 71, cooperating with the second locking member 72, is configured to rotate the sleeve during sliding of the shield 30 and to lock the shield 30 in the locking position.

More in detail, the first locking member 71 cooperates with the second locking member 72 for guiding the shield 30 from the initial position to the locking position passing through the intermediate position. Furthermore, the first locking member 71 and the second locking member 72 cooperate to lock the shield 30 in the locking position when the shield 30 reaches the locking position.

Preferably, the first locking member 71 is formed on the inner surface 31 of the shield 30 while the second locking member 72 is formed on the outer surface 62 of the sleeve 60.

According to one embodiment, the second locking member 72 comprises a slit 73 and the first locking member 71 comprises a pin 74 configured to engage the slit 73.

Preferably, the slit 73 comprises a first stopping member 73a, a second stopping member 73b and a locking member 73c which are configured to longitudinally limit the sliding of the shield 30.

Specifically, the first stopping member 73a is configured to engage the pin 74 in the initial position of the shield 30 to prevent longitudinal sliding of the shield 30 toward the distal end 21 of the needle 20. In contrast, the second stopping member 73b is configured to engage the pin 74 in the intermediate position of the shield 30 to prevent longitudinal sliding of the shield 30 toward the proximal end 22 of the needle 20. It is to be noted that the first stopping member 73a and the second stopping member 73b are configured to limit the stroke of the shield 30 along the longitudinal axis. As a matter of fact, the first stopping member 73a retains the shield 30 against preloaded elastic force of the elastic member 50 which urges the shield 30 toward the distal end 21, while the second stopping member 73b is configured to stop the shield 30 at the intermediate position during the injection.

The locking member 73c is configured to engage the pin 74 in the locking position of the shield 30 to prevent longitudinal sliding of the shield both toward the distal end 21 and the proximal end 22 of the needle 20. Specifically, the locking member 73c is configured to retain the pin 74 in order to prevent further use of the safety needle device 1 and the sliding of the shield along the longitudinal direction. Preferably, also the locking member 73c limits the stroke of the of the shield 30 along the longitudinal axis X-X, retaining the shield 30 against preloaded elastic force of the elastic member 50 which continues to urge the shield 30 toward the distal end 21 also in the locking position. More preferably, the locking member 73c has "C" shape which is configured to receive and hold the pin 74 avoiding further sliding of the shield 30 when the pin 74 reach the locking member 73c.

According to one embodiment, the slit 73 further comprises a first rotation member 73d and a second rotation member 73e which are configured to convert the longitudinal sliding of the shield 30 into a rotation of the sleeve 60. Specifically, the first rotation member 73d and the second rotation member 73e engage the pin 74 in order to rotate the sleeve 60.

In detail, the first rotation member 73d is configured to engage the pin 74 and rotate the sleeve 60 upon sliding of shield 30 along the longitudinal axis X-X from initial position toward the intermediate position. In contrast, the second rotation member 73e is configured to engage the pin 74 and rotate the sleeve 60 upon sliding of the shield 30 along the longitudinal axis X-X from the intermediate position toward the locking position. In other words, the first rotation member 73d provides a first rotation of the sleeve 60 around the longitudinal axis X-X during the injection while the second rotation member 73e provides a second rotation of the sleeve 60 around the longitudinal axis X-X during the extraction.

Preferably, the rotation of the sleeve 60 allows the passage of the pin from the first stopping member 73a to the locking member 73c to longitudinally lock the shield 30.

More preferably, the slit 73 further comprises further comprises a guide member 73f configured to engage the pin 74 and avoid the rotation of the sleeve 60 for at least a portion of the sliding of the shield 30 along the longitudinal axis X-X. Specifically, during the injection the pin 74 after the first rotation of the sleeve engages the guide member 73f until the second stopping member 73b reaching the intermediate position of the shield 30. Subsequently, during the extraction, the pin 74 constantly engages the guide member 73f until it reaches the second rotation member 73e which allows the second rotation of the sleeve 60.

The invention claimed is:

1. A safety needle device, comprising:
    a hub configured to be connected to a vessel;
    a needle attached to the hub, the needle extending along a longitudinal axis between a distal end, configured for insertion into a patient, and an opposed proximal end, configured for connection to the vessel;
    a shield slidable relative to the hub along the longitudinal axis and rotationally constrained around the longitudinal axis, wherein the shield is irreversibly slidable from an initial position, before injection, to a locking position, after injection, passing through an intermediate position;
    a housing attached to the hub and surrounding:
        a portion of the hub;
        a portion of the shield when the shield is in the initial position and in the locking position; and
        almost totally the shield when the shield is in the intermediate position;
    an elastic member arranged within the housing and acting on the shield, wherein the elastic member is biased to push the shield toward the distal end of the needle and to resist a longitudinal sliding of the shield toward the proximal end of the needle;
    a sleeve arranged within the housing and rotatably mounted around the longitudinal axis relative to the shield and the housing; and
    a locking arrangement comprising at least one first locking member formed on the shield and at least one second locking member formed on the sleeve, the at least one first locking member cooperating with the at least one second locking member to:
  rotate the sleeve upon sliding of the shield for guiding the shield from the initial position to the locking position; and
  lock the shield in the locking position when the locking position is reached;
wherein the shield surrounds:
  at least partially the sleeve when the shield is in the initial position and in the locking position; and
  almost totally the sleeve when the shield is in the intermediate position; and
wherein the safety needle device further comprises a guiding arrangement comprising first guiding members formed on the shield and second guiding members formed on the housing, the first guiding members cooperating with the second guiding members to guide the sliding of the shield along the longitudinal axis and to prevent rotation of the shield relative to the housing.

2. The safety needle device of claim 1, wherein the housing has an inner surface, at least partially facing the sleeve and the shield, and an opposed outer surface,
  wherein the shield has an outer surface at least partially facing the inner surface of the housing and an inner surface at least partially facing the sleeve, and
  wherein the sleeve has an inner surface at least partially facing the hub and an opposite outer surface at least partially facing the inner surface of the shield and the inner surface of the housing.

3. The safety needle device of claim 2, wherein the first guiding members are formed on the outer surface of the shield, and
  wherein the second guiding members are formed on the inner surface of the housing.

4. The safety needle device of claim 2, wherein the second guiding members comprise longitudinal grooves formed on the inner surface of the housing, and
  wherein the first guiding members comprise protrusions projecting from the outer surface of the shield, that are configured to engage the longitudinal grooves.

5. The safety needle device of claim 2, wherein the first guiding members are angularly spaced apart on the outer surface of the shield, and
  wherein the second guiding members are angularly spaced apart on the inner surface of the housing.

6. The safety needle device of claim 2, wherein the at least one first locking member is formed on the inner surface of the shield, and
wherein the at least one second locking member is formed on the outer surface of the sleeve.

7. The safety needle device of claim 6, wherein the at least one second locking member comprises a slit, and
  wherein the at least one first locking member comprises a pin configured to engage the slit.

8. The safety needle device of claim 7, wherein the slit comprises:
  a first stopping member configured to engage the pin in the initial position of the shield to prevent longitudinal sliding of the shield toward the distal end of the needle;
  a second stopping member configured to engage the pin in the intermediate position of the shield to prevent the longitudinal sliding of the shield toward the proximal end of the needle; and
  a third locking member configured to engage the pin in the locking position of the shield to prevent the longitudinal sliding of the shield toward both the distal end and the proximal end of the needle.

9. The safety needle device of claim 7, wherein the slit comprises:
  a first rotation member configured to engage the pin and to rotate the sleeve upon the sliding of the shield along the longitudinal axis from the initial position toward the intermediate position; and
  a second rotation member configured to engage the pin and to rotate the sleeve upon the sliding of the shield along the longitudinal axis from the intermediate position toward the locking position.

10. The safety needle device of claim 2, wherein the elastic member at least partially surrounds the outer surface of the sleeve, and
  wherein the elastic member is interposed between the hub and the shield.

11. The safety needle device of claim 10, wherein the elastic member extends between a distal portion and a proximal portion along the longitudinal axis,
  wherein the hub comprises a stop wall configured to accommodate the proximal portion of the elastic member, and
  wherein the shield comprises an annular flange projecting from the inner surface of the shield and configured to retain the distal portion of the elastic member.

12. The safety needle device of claim 2, wherein the shield comprises a sign on the outer surface of the shield, and
  wherein the sign is configured to be visible only when the shield is in the locking position.

* * * * *